United States Patent
Sponchia et al.

(10) Patent No.: US 10,501,331 B2
(45) Date of Patent: Dec. 10, 2019

(54) TOTALLY-MESOPOROUS ZIRCONIA NANOPARTICLES, USE AND METHOD FOR PRODUCING THEREOF

(71) Applicant: BRENTA S.R.L., Montecchio Maggiore (IT)

(72) Inventors: Gabriele Sponchia, Noventa di Piave (IT); Alvise Benedetti, Venice (IT); Pietro Riello, Padua (IT)

(73) Assignee: BRENTA S.R.L., Montecchio Maggiore (IT)

( * ) Notice: Subject to any disclaimer, the term of this patent is extended or adjusted under 35 U.S.C. 154(b) by 0 days.

(21) Appl. No.: 15/547,122

(22) PCT Filed: Jan. 27, 2016

(86) PCT No.: PCT/IB2016/050394
§ 371 (c)(1),
(2) Date: Jul. 28, 2017

(87) PCT Pub. No.: WO2016/120795
PCT Pub. Date: Aug. 4, 2016

(65) Prior Publication Data
US 2018/0022615 A1 Jan. 25, 2018

(30) Foreign Application Priority Data

Jan. 28, 2015 (IT) .............................. PD2015A0015

(51) Int. Cl.
| | | |
|---|---|---|
| *A61K 31/704* | (2006.01) | |
| *A61K 31/4745* | (2006.01) | |
| *A61K 9/14* | (2006.01) | |
| *A61K 41/00* | (2006.01) | |
| *C01G 25/02* | (2006.01) | |
| *A61K 9/00* | (2006.01) | |
| *A61K 8/28* | (2006.01) | |
| *A61Q 19/00* | (2006.01) | |
| *A61K 8/02* | (2006.01) | |
| *A61K 9/51* | (2006.01) | |

(52) U.S. Cl.
CPC .............. *C01G 25/02* (2013.01); *A61K 8/025* (2013.01); *A61K 8/0279* (2013.01); *A61K 8/28* (2013.01); *A61K 9/00* (2013.01); *A61K 9/143* (2013.01); *A61K 31/4745* (2013.01); *A61K 31/704* (2013.01); *A61K 41/0057* (2013.01); *A61Q 19/00* (2013.01); *A61K 9/5115* (2013.01); *A61K 2800/10* (2013.01); *A61K 2800/412* (2013.01); *A61K 2800/413* (2013.01); *A61K 2800/56* (2013.01); *C01P 2004/03* (2013.01); *C01P 2004/04* (2013.01); *C01P 2004/32* (2013.01); *C01P 2004/61* (2013.01); *C01P 2004/62* (2013.01); *C01P 2004/64* (2013.01); *C01P 2006/12* (2013.01); *C01P 2006/13* (2013.01)

(58) Field of Classification Search
CPC .. A61K 31/00; A61K 31/704; A61K 31/4745; A61K 9/00; A61K 9/143; A61K 9/5115
See application file for complete search history.

(56) References Cited

U.S. PATENT DOCUMENTS

2010/0051877 A1 3/2010 Wei et al.

FOREIGN PATENT DOCUMENTS

WO 1997043040 A1 11/1997

OTHER PUBLICATIONS

Tang et al., "Hollow Mesoporous Zirconia Nanocapsules for Drug Delivery," Advanced Functional Materials 20(15):2442-2447 (2010).
Chen et al., "Facile Synthesis of Monodisperse Mesoporous Zirconium Titanium Oxide Microspheres with Varying Compositions and High Surface Areas for Heavy Metal Ion Sequestrian," Advanced Functional Materials 22(9)1966-1971 (2012) (wih supporting information).
Wang et al., "Mesoporous Titanium Zirconium Oxide Nanospheres with Potential for Drug Delivery Applications," ACS Applied Materials and Interfaces 5:10926-10932 (2013) (with supporting information S1-S5).
International Search Report and Written Opinion corresponding to PCT/IB2016/050394, dated May 6, 2016.

*Primary Examiner* — Zohreh A Fay
(74) *Attorney, Agent, or Firm* — Pepper Hamilton LLP

(57) ABSTRACT

The present invention relates to novel totally-mesoporous zirconium oxide nanoparticles as well as a sol-gel synthesis process thereof which include an innovative nanoparticles purification step. Said nanoparticles are characterized by a totally-mesoporous structure i.e. a distribution of pores within the so-called the mesoporous range uniformly distributed throughout the entire nanoparticle volume. Furthermore, said nanoparticles are non-cytotoxic and present a high surface area, which make particularly suitable in both biomedical and industrial applications (e.g. drug delivery, heavy metals ion sequestration). The manufacturing method is simple and advantageously allows for high control over the shape and diameter of the nanoparticles as well as over the nanoparticles pores.

27 Claims, 5 Drawing Sheets

(a)

(b)

(a)

(b)

(a)

(b)

(a)

(b)

(a)

(b)

TOTALLY-MESOPOROUS ZIRCONIA NANOPARTICLES, USE AND METHOD FOR PRODUCING THEREOF

This application is a national stage application under 35 U.S.C. § 371 of PCT Application No. PCT/IB2016/050394, filed Jan. 27, 2016, which claims priority of Italy Application No. PD2015A000015, filed Jan. 28, 2015, which are hereby incorporated by reference in their entirety.

TECHNICAL FIELD

The scope of the present invention relates to nanoparticles made of zirconium oxide ($ZrO_2$), a compound commonly referred to as 'zirconia'. More specifically, the invention describes and claims inventive concepts relevant to new $ZrO_2$ nanoparticles characterized by an amorphous and mesoporous structure. Particularly, the scope of the present invention encompasses a manufacturing method which allows to produce high-purity grade zirconia nanoparticles of substantially spherical shape, characterized by a totally-mesoporous structure, i.e. a distribution of pores within the so-called mesoporous range, uniformly distributed throughout the entire nanoparticle volume.

BACKGROUND ART

In the last decades, mesoporous nanoparticles have been a topic of intense research because of the many potential applications that can be developed by taking advantage of their high surface area. Actually, these nanoparticles present pores sizes between 2 to 50 nm (and are thus called 'mesoporous' according to IUPAC nomenclature), an ideal characteristic in all those applications where a high surface interaction is essential, for example in biomedical applications (e.g. drug delivery or imaging), in the catalysis and filtration (e.g. heavy metals ion sequestration), in sensor devices (e.g. gas sensor) or in cosmetics, just to name a few application fields. Indeed, the presence of pores in the mesoporous range allows the nanoparticles to be loaded with organic molecules such as enzymes, active substances or inorganic nanometric phases having catalytic, magnetic or optical properties. Normally, mesoporosity of the nanoparticle is intimately associated with an amorphous structure because a crystalline structure generally leads to the closure of the pores.

The intense research in the recent years has been substantially devoted to achieve an increasingly better control of the particles at a micro and nano level, and particularly of their physical-chemical and electronic properties. This goal represents the starting point for developing new materials with highly selective functions, or new multifunctional materials, which are able to meet the requirements of different applications e.g. in nanomedicine. This quest in turn encourages research for oxides which can be synthesized in the form of mesoporous nanoparticles.

Among the oxides, silica have been mainly used so far because the synthesis of stable mesoporous silica nanoparticles (or MSNs) is relatively ease to achieve: a process for synthesizing MSNs based on the sol-gel technique was first developed in Japan in 1990 and later at the Mobil Corp. Laboratories in the US.

Other metal oxide compositions of mesoporous nanoparticles have been described extensively in both the scientific and patent literature such as titanium oxide, yttrium oxide, barium oxide as well as several mixed oxides. For example, Fu and Watson in US20130122298 describes a process for synthesizing a titanium oxide in the form of spherical nanoparticles mesoporous with a diameter between 20-100 nm. In the patent application US20140170088A1 it is disclosed a process for synthesizing nanoparticles of barium oxide and zirconium $BaZrO_3/BaCO_3$ useful in the formulation of coatings for biomedical applications. However such methods are not useful to produce zirconia nanoparticles. Often, the metal oxides nanoparticles already known to the state-of-the-art have a low surface to volume ratio, or a low surface electrical charge, or other characteristics which make them not suitable in many applications especially in the biomedical field. This represents a significant drawback that encourages the search for new compositions and consequently for synthesis processes. However, taking aside silica, it is definitely not a simple task the synthesis of metal oxides mesoporous well-separated nanoparticles with a controlled shape and size. The main challenge to overcome is controlling the reactivity of certain intermediates or metal oxides precursors used in the process.

In the present case, the properties of zirconium oxide (or zirconia) nanoparticles, have been described extensively in both the scientific papers and patents. However, nanoparticles known in the state-of-the-art have a crystalline structure which make them non-optimal in those applications where the high specific surface area represent a crucial factor, as in drug delivery, in catalysis or in the treatment of water.

Most relevant for assessing the novelty and the inventive step of the present invention are the following three prior-art documents.

The first paper by Chen et al. '*Facile Synthesis of Monodisperse Mesoporous Zirconium Titanium Oxide Microspheres with Varying Compositions and High Surface Areas for Heavy Metal Ion Sequestration*' (DOI: 10.1002/adfm.201102878) describes mesoporous microspheres of zirconia-titania ($ZrO_2$—$TiO_2$) binary oxides with different $TiO_2$ contents prepared by sol-gel method. Noticeably, the process proposed by Chen et al. allows also to synthesize microspheres of pure zirconia. However, such particles present a crystalline structure (while binary oxides zirconia-titania microspheres are amorphous) and are characterized by a limited surface area. Furthermore, said pure zirconia microspheres are clusters of aggregated distinct entities of about 3.5 nm in size. Finally, in the paper by Chen et al. the microspheres purification step includes calcination at high temperature (i.e. around 600° C.) that degrades the mesoporous structure.

Although this paper describes a remarkable achievement in the field, due to these drawbacks it contains no useful teachings for those skilled in the art for synthesizing mesoporous nanoparticles composed of pure zirconium oxide having the formula $ZrO_2$.

The second relevant paper is '*Hollow Mesoporous Zirconia Nanocapsules for Drug Delivery*' by Shaoheng Tang et al. (in Adv. Funct. Mater. 2010, 20, 2442-2447), concerns the synthesis of a very special class of nanoparticles called hollow mesoporous zirconia nanocapsule and their use as drug delivery carrier. These nanoparticles have a microstructure constituted by a spherical cavity (larger than 100 nm) delimited by a mesoporous zirconia shell with a thickness of a few nanometers (approximately 15 nm). For this reason, the authors name them 'hollow nanocapsules'. In the hollow nanocapsule described by Shaoheng Tang et al. the mesoporosity is obviously limited to the thin zirconia shell, since the internal cavity exceeds the superior limit according to the IUPAC mesoporous definition (50 nm).

It is evident that hollow nanocapsules present a totally different structure from particles having a mesoporous structure extending throughout the entire particle volume (and not throughout only the shell). Such particles are named 'totally-porous' or 'totally-mesoporous' nanoparticles. For the sake of clarity, the present invention relates to 'totally-porous particles' and more specifically to 'totally-porous nanoparticles'.

In the work by Shaoheng Tang et al. nanocapsules fabrication is based on a process which uses Stöber silica spheres coated with a layer of mesoporous zirconia. After a thermal treatment, that is needed to consolidate the zirconia layer, the sacrificial silica core is removed by means of a treatment in NaOH solution so that the capsules are created. It is evident that such method cannot be used to prepare totally porous nanospheres or, more generally, particles without a large internal cavity. In fact, the spherical shape of the hollow nanocapsules is due to the shape of the spherical silica sacrificial template.

Noticeably, the authors remark that the energy dispersive X-ray spectrum (EDX) of the prepared hollow nanocapsules shows a small amount of silica remaining in the porous zirconia shell. The presence of residual silica have a significant impact on the isoelectric point of the nanocapsules and should be avoided.

The peculiar structure of hollow mesoporous zirconia nanocapsule make them suitable as drug carrier because the spherical cavity can accommodate a large amount of drug. However, drug-loading capacity and efficiency depends tightly on the compatibility between the loaded molecules and the particle carrier, and molecules characteristic such as polarity, hydrophobicity, and surface charge distribution as well as charge distribution of the carrier often affect compatibility. For this reason, the loading mechanism in hollow mesoporous zirconia nanocapsule and in totally-mesoporous nanoparticle are completely different: in the first case, the drug are accommodated in the central cavity, whereas, in the latter, the drug is loaded inside the pores where there is a strong interaction with the internal pores surface. Obviously, the loading mechanism affects also the release mechanism of the drug.

Finally, the third relevant document is the US patent 2010/051877, 'Superficially porous metal oxide particles, methods for making them, and separation devices using them' in the name of Ta-Chen Wei et al. In this case, the authors disclose superficially porous particles composed of metal-oxide (i.e. silica, alumina, titania or zirconia) and the preparation thereof. Such superficially porous particles comprise; a solid core having a size ranging from about 20% to about 90% of the size of the entire particle; a substantially porous outer shell having ordered pores. Interestingly, the authors remark the difference between 'totally porous particles' and 'superficially porous particles' and they conclude that the latter are more suitable for chromatography applications.

Therefore, it is clearly out of the scope of the invention preparing 'totally-mesoporous' metal-oxide particles as the purpose of the inventors is disclosing a novel core-shell structure, wherein only the shell is porous, suitable for chromatography applications. Furthermore, the inventors claim, but not provide, any example of superficially porous particles made of zirconia. For the aforementioned reasons, it will be apparent to those skilled in the art that similarly to the work by Shaoheng Tang et al., US2010/051877 does not disclose any useful teaching for preparing 'totally-mesoporous' zirconia particles and nanoparticles.

To sum up, the main technical problem which has prevented so far the synthesis of mesoporous zirconium oxide nanoparticles is the much higher reactivity of the zirconia organic precursors (alkoxides) compared to those used in the synthesis of mesoporous silica nanoparticle. For this reason, synthesis routes based on sol-gel techniques, which yield zirconia nanoparticle starting from alkoxides, are very unstable and therefore difficult to control. Nevertheless, sol-gel techniques are attractive due to their simple operation and widely available literature.

A second problem in the synthesis of mesoporous zirconia nanoparticles concerns the purification step that is required to remove any residual surfactant or other organic solvents used in the synthesis. Generally, metal-oxide nanoparticles purification involves thermal treatments, e.g. calcination in an oven at high temperature, or washing cycles with strong acids, e.g. hydrochloric acid. The first technique is commonly used for mesoporous silica nanoparticles as the structure of the amorphous silica is stable to calcination temperatures (around 500-600° C.). The second technique, can be used only when the nanoparticles are not dissolved on acid washing. However, these known purification treatments cannot be used to purify amorphous zirconia nanoparticles because in the temperature range required for surfactant degradation, zirconia changes from an amorphous to a crystalline phase, and unfortunately, this phase transition leads to the closure of the pores in the structure. In addition zirconia particles are etched by acid washing.

DISCLOSURE OF INVENTION

Technical Problem

From the above discussion, it should be clear that it is desirable to have a large range of nanostructures, including totally-mesoporous zirconia nanoparticles, to meet the requirements of a number of fields and particularly nanomedicine. Clearly, the lack of a readily-available process for manufacturing such zirconia nanoparticle represents a serious limitation especially in bio-medical applications where high-purity and size control of the nanoparticles are crucial requirements.

In view of the above drawbacks of the prior art, in a number of demanding applications (e.g. nanomedicine) there is still a need for zirconium oxide ($ZrO_2$) nanoparticles having a stable totally-mesoporous structure and also for a simple producing method thereof. Particularly, there is still a need for a producing method, based on the sol-gel technique, which allows the synthesis and purification of $ZrO_2$ nanoparticles with an improved purity grade and which also allows control over the structure i.e. the shape and the dimension of said nanoparticles, the pores shape and the pores distribution within the mesoporous range.

Consequently, the present invention intends to overcome the disadvantages existing in the prior art related to $ZrO_2$ nanoparticles technology.

Solution to Problem

Technical Solution

Accordingly, it is a first object of the present invention to provide a zirconium oxide in the form of totally-mesoporous nanoparticles or microparticles having a substantially spherical shape, as set forth in the appended independent claim. Said zirconium oxide particles are characterized by a totally-mesoporous structure i.e. by a generally uniform and stable pore distribution throughout the entire particle volume.

Particularly, it is a second object of the present invention to provide zirconium oxide mesoporous nanoparticles or microparticles with an improved purity compared to prior art materials and particularly with no residual of the synthesis process, e.g. residual of the sacrificial templating materials.

Still, a third object of the present invention is to provide a nanosystem obtained by functionalizing or loading said zirconium oxide particles with organic molecules, organometallic or inorganic phases, or to provide materials obtained by dispersing said zirconium oxide particles into a resins or other medium so as to meet specific needs, particularly in nanomedicine.

It is a fourth important object of the present invention to provide a simple and easy-to-control production process for said zirconium oxide totally-mesoporous nanoparticles or microparticles as set forth in the appended independent claim. Said process is based on a alkoxides-derived sol-gel technique and, according to specific needs, allows for tailoring dimension and mesoporous structure of said particles by conveniently varying process parameters such as the concentration, pH and type of precursors.

Still, it is a fifth object of the present invention to provide a production process which yields zirconium oxide totally-mesoporous well-separated particles i.e. present a reduced aggregation compared to prior art particles so that they can be easily dispersed by means of well-known techniques.

Finally, it is a last object of the present invention to disclose the use of said totally-mesoporous nanoparticles or microparticles in some applications, e.g. as a carrier for drug-delivery, as described in the appended independent claims.

In view of the above disadvantages or drawbacks of the prior art, the present inventors have made a lot of studies related to the preparation of mesoporous nanoparticles via a sol-gel technique. These studies were mainly directed to address the notorious instability of alkoxides, and thus to achieve control over the nanoparticle dimension and mesoporous structure.

After long terms of practice and a lot experiments the inventors found a novel zirconium oxide having formula $ZrO_2$ in the form of nanoparticles, of generally spherical shape, characterized by a totally-mesoporous structure with a specific surface area of more than about 200 $m^2/g$. Noticeably, said mesoporous structure is distributed throughout the entire volume of said particle without any inner cavities (except those due to mesoporosity). The new zirconium oxide were prepared from alkoxide precursor using a modified sol-gel technique which allows to control the nanoparticle dimension and mesoporous structure as well as the purity of the nanoparticles.

Advantageous Effects of Invention

Advantageous Effects

The mesoporous zirconium oxide nanoparticles according the present invention have a number of remarkable advantages which are listed in the following:
 The zirconia nanoparticles present a mesoporous structure distributed throughout the entire volume of said particle (i.e. they are totally-mesoporous nanoparticles) with a specific surface area of more than about 200 $m^2/g$. The high specific surface area allows to load doxorubicin with a loading capacity of about 100 mg/g;
 The novel nanoparticles are constituted by pure zirconium oxide $ZrO_2$ with no residual of alkaline halide and sacrificial templating materials (i.e. surfactant). This is a clear advantage, because the presence of process residual may affect properties such as surface charge and isoelectric point of the nanoparticles. More importantly, the high-purity grade of the nanoparticles make them non-cytotoxic as in vivo tests in mice showed;
 The novel nanoparticles can be easily functionalized or loaded with active molecules (e.g. a drug or a fluorescent dye), and they are easily dispersible in a medium (e.g. a biopolymer), so as to prepare a biocompatible bio-system, or a biocompatible material comprising said nanoparticles and/or said nano-bio system. By producing customized nano-bio systems and materials, a number of fields can benefit from the advantageous properties of the novel nanoparticles; just to mention a few: nanomedicine, regenerative medicine and prosthetics, dentistry, cosmetics, groundwater and process water treatment, sensors.

In addition, the method of the present invention has several advantages with respect to the methods known in the art:
 The purification of nanoparticles is based on the vacuum sublimation of the organic residues and occurs at temperatures much lower compared to traditional calcination process. This achievement allows the production of high-purity mesoporous zirconia nanoparticles without reducing the specific surface area or, worse, damaging the entire mesoporous structure. For this feature, the nanoparticles according to the present invention are particularly suitable in the medical and biomedical applications;
 The method provides several mechanisms for tailoring the nanoparticle size and the pore size (e.g. by varying the alkaline halide added in the solutions), in view of the functions sought for the nano-biosystem and according to the size of the particles and/or molecules to be loaded. This represents a remarkable advantage, especially in the biomedical field, since the size of the particles plays an important role in defining the bio-distribution and thus the application range;
 Finally, the production method is easy and scalable allowing for a simplification of the synthesis plant layout, in a better process control and in cost-saving. These advantages lead to a improved flexibility and ease in the production of the nanoparticles on an industrial scale.

Additional objects and advantages of the invention will be set forth in part in the description which follows, and in part will be obvious from the description, or may be learned by practice of the invention. It will apparent to those skilled in the art that the advantages of the present invention can not be achieved by prior art zirconium oxide nanoparticles.

BRIEF DESCRIPTION OF DRAWINGS

Description of Drawings

Figure 1:
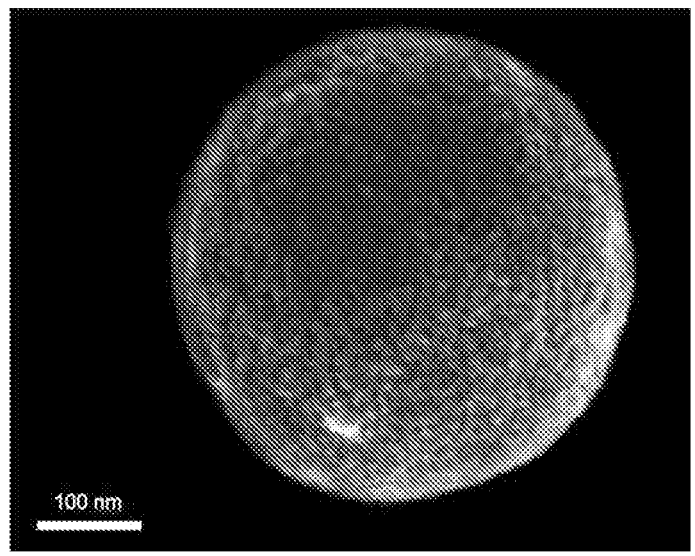
Figure 1:
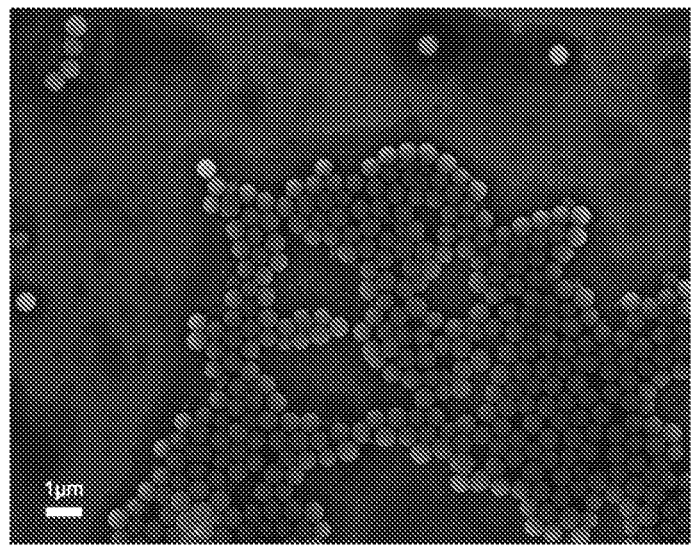
Figure 2:
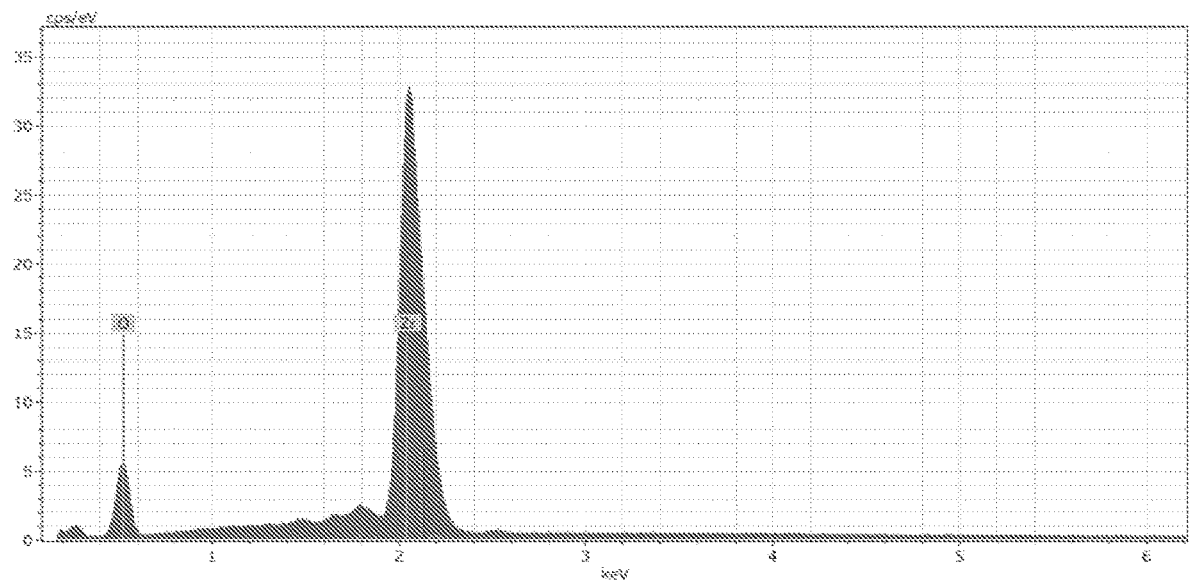
Figure 2:
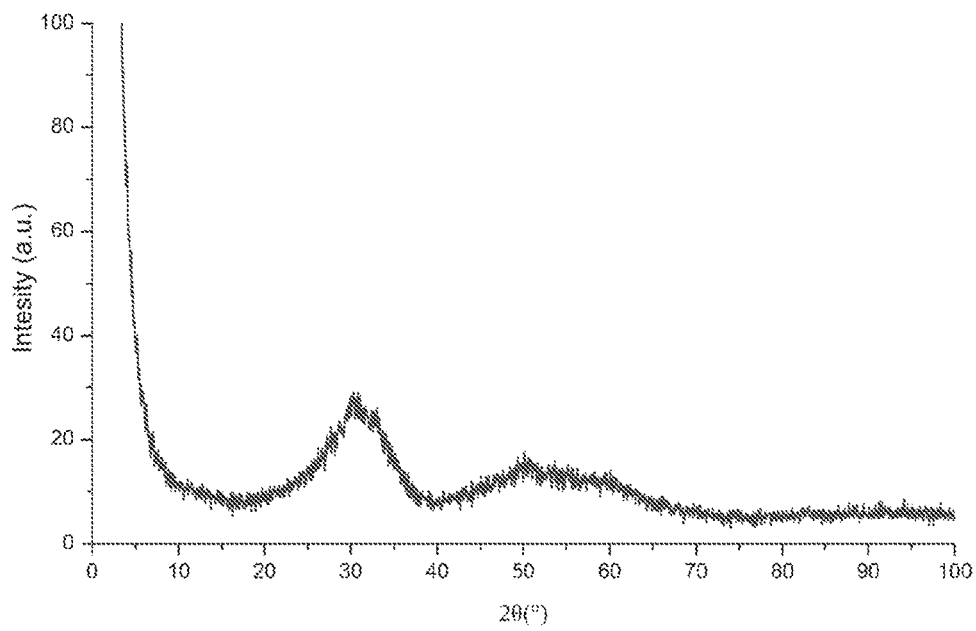
Figure 3:
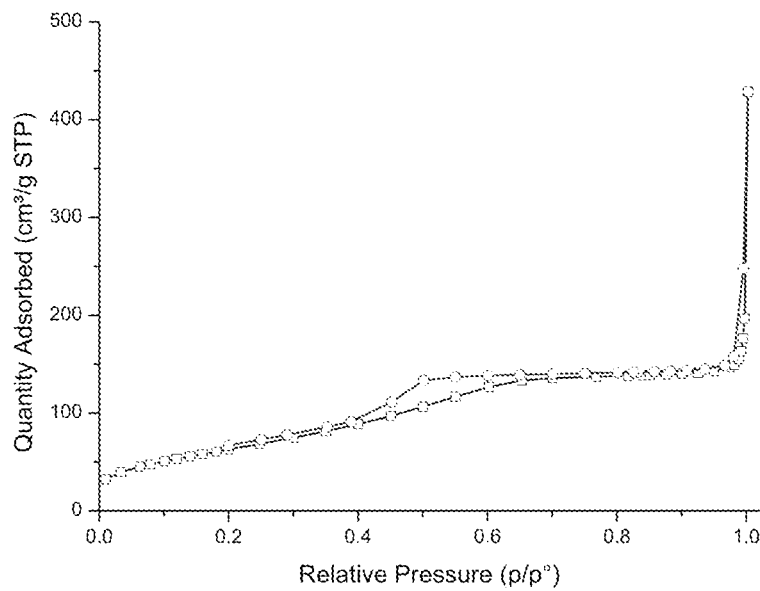
Figure 3:
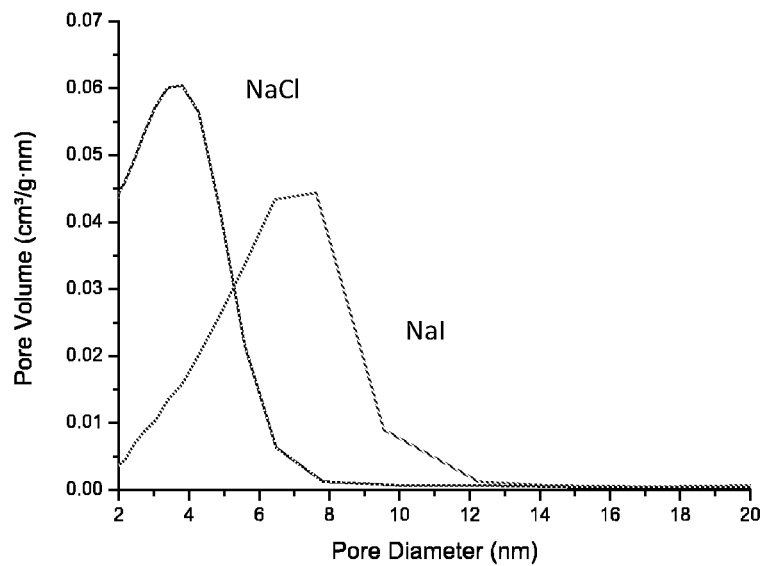

The present invention will be more fully understood by reference to the following drawings which are for illustrative purposes only:

FIG. 1 shows SEM images of the $ZrO_2$ mesoporous nanoparticles according to the best mode of the present invention. Particularly, (a) shows a single $ZrO_2$ nanoparticle, while (b) a plurality of $ZrO_2$ nanoparticles;

FIG. 2 referring to Example 1 according to the best mode of the present invention, shows in: (a) EDX (Energy Dispersive X-ray) spectrum and in (b) XRPD (X-Ray Powder Diffraction) pattern;

FIG. 3 shows, for two nanoparticles samples according to the present invention, in (a) the $N_2$ absorption/desorption isotherms, while in (b) the pore size distributions according to the BJH method (in this case, the measured specific surface area is 240 $m^2/g$).

Figure 4:
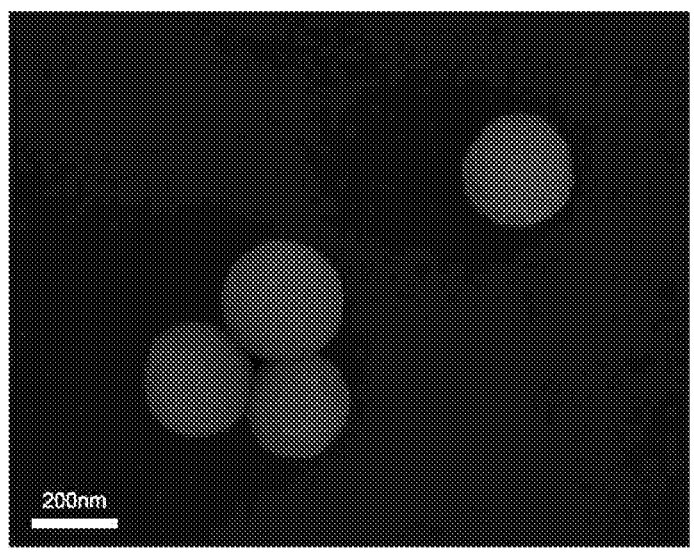
Figure 4:
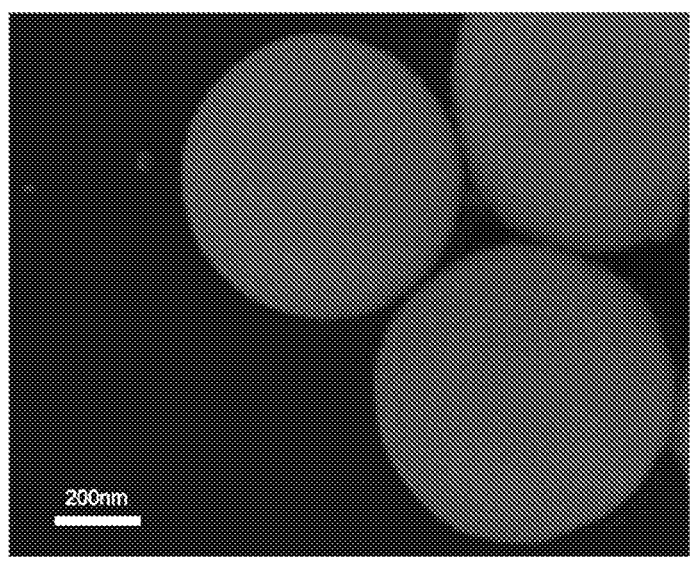
Figure 5:
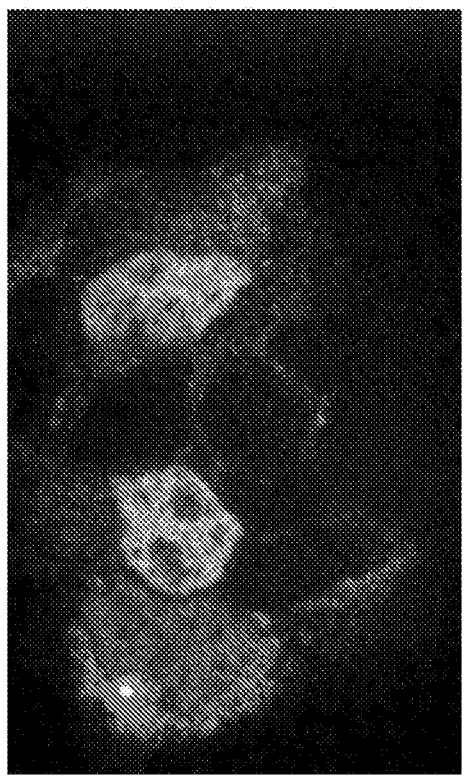
Figure 5:
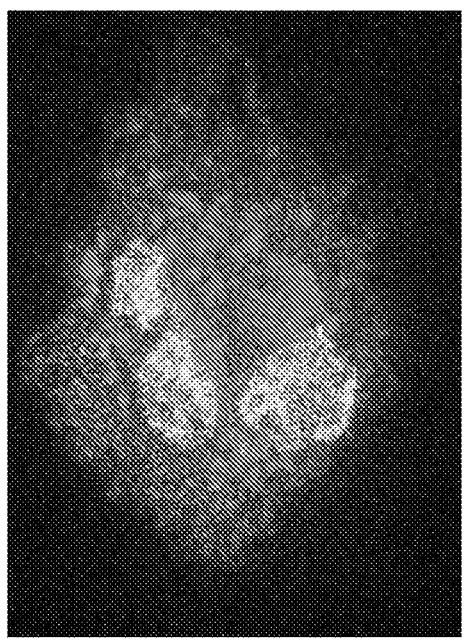

FIG. 4 shows SEM images of the nanoparticles according to the present invention having different diameters, in (a) about 200 nm while in (b) about 500 nm. Nanoparticle diameter was altered by tuning in a controlled way the process parameter of the production method;

FIG. 5 shows confocal microscopy images of a cell with the $ZrO_2$ nanoparticles according to the present invention inside the cell cytoplasm (nanoparticles appear as red dots; the green areas represent the cell nuclei not penetrated by nanoparticles).

These figures illustrate and demonstrate various features and embodiments of the present invention, and of the manufacturing method thereof, but are not to be construed as limiting the invention.

MODE FOR THE INVENTION

Mode for Invention

DETAILED DESCRIPTION OF THE INVENTION

For the purpose of understanding the specification and the appended claims, in the following description the chemical elements are defined by means of the respective symbols as reported in a common periodic table of elements. For example, hydrogen is represented by its symbol H; helium is represented by He and so on. Also, it is to be understood that the chemical symbol comprises all isotopes and ions unless stated otherwise. Again, for the sake of brevity, the chemical compounds may be indicated by acronyms widely adopted in the technical field related to the present invention. Similarly, the term 'zirconia' will mean the zirconium oxide or in formula $ZrO_2$.

For the sake of clarity, the term 'particle' as used in the description and in the claims of the present invention shall designate an aggregate of atoms, molecules or other fundamental constituents, such aggregate having sub-micrometric size or super-micrometric and a substantially spherical shape but also a non-symmetrical shape. Particularly, the terms 'nanoparticle' or 'nanostructure', singular or plural, shall indicate exclusively a particle of size less than about 1 micrometer.

In addition, the term 'mesoporous' as used herein shall refer to particles (according to the definition provided above) having pore diameters comprised between 2 to 50 nm. Particularly, the term 'total mesoporous' or 'totally-mesoporous' shall mean a mesoporous particle having a mesoporous structure which extends throughout the entire particle volume and which does not limit only to part of the particle, e.g. the particle shell.

Also, the term 'bio-nano system' as used herein shall indicate a system, not necessarily of sub-micrometer size, wherein one or more organic molecules, macromolecules, organometallic compounds or inorganic phases are chemically bound or adsorbed to one or more particles, or are loaded into the pores of said particles.

Furthermore, the phrases 'well-separated' or 'reduced aggregation' particles as used herein shall mean a set of particles having sub-micrometric size or super-micrometric, and which do not form stable aggregates of two or more particles and therefore can be easily dispersed in a medium or separated from each other by means of standard techniques, e.g. with ultrasound sonication, centrifugation or filtration.

Finally, the term 'about' as used herein is intended to include values, particularly within 10% of the stated values. The use of 'or' means 'and/or' unless stated otherwise. It is to be understood that the detailed description is for the purpose of fully disclosing preferred embodiments of the invention without placing limitations thereon.

Best Mode for Carrying out the Invention

By way of example, but not limitation, FIG. 1(a) shows the SEM image of a nanoparticle according to the present invention having a substantially spherical shape and a diameter equal to about 500 nm. Similarly, the FIG. 1(b) shows a plurality of said nanoparticles and demonstrate the low dispersion in size distribution and that they are well-separated particles.

Furthermore, from the EDX spectrum of FIG. 2 (a), it will be apparent to those skilled in the art that said nanoparticles are composed of zirconium (Zr) and oxygen (O) in the expected stoichiometric ratio 1 to 2. Therefore said nanoparticles, whose producing method will be disclosed later, are actually constituted by zirconium oxide $ZrO_2$ with no residual of alkaline halide and sacrificial templating materials (amine nonionic surfactant).

In addition, by way of illustration rather than by limitation of the invention set forth in the claims, FIG. 2(b) shows the XRPD diffraction spectrum (CuK a radiation) from powders consisting of the same nanoparticles as those illustrated in FIG. 1. The skilled in the art will find evident how this XRDP spectrum is characteristic of an amorphous material and therefore of pure zirconium oxide $ZrO_2$ in amorphous form. In fact, it is well-known that pure zirconium oxide $ZrO_2$ in crystalline form has a totally different XRDP spectrum which is characterized by a number of well-defined narrow peaks at wavelengths which are strictly dependent on the crystallographic structure.

Finally, the $N_2$ absorption/desorption isotherms of FIG. 3 (a), herein provided as a non-limitative example, shows that the nanoparticles according to the present invention have a mesoporous structure (type IV according to the IUPAC classification). Such mesoporous structure is characterized by homogeneously distributed pores with the pore size distributions (obtained by the BJH method) presented in FIG. 3(b). Specifically, with reference to the two samples provided, the pores size is about 4 nm and about 8 nm and the specific surface area is about 240 $m^2/gr$ (other features of these samples will be presented later in the examples).

In this way, it has been disclosed a pure zirconium oxide ($ZrO_2$) in the form of mesoporous nanoparticles, thus achieving one of the main tasks of the present invention.

In the best mode of the present invention, the mesoporous nanoparticles of pure zirconium oxide ($ZrO_2$) are advantageously produced by means of a new and inventive modification of the sol-gel technique. The process steps are described in the following by way of example, but not limitation.

Step 1: Preparation of the Surfactant Solution and Micelles Formation

The process begins by dissolving in ethanol a surfactant, preferably hexadecylamine or other amine nonionic surfactant e.g. a primary amine having an alkyl or a long aliphatic chain. Advantageously the ratio between the hexadecylamine and the ethanol varies in a range between about 1:200 v/v to about 1:800 v/v.

The solution is then mixed with a solution of an alkaline halide and deionized water in an amount suitable for the hydrolysis reaction to start. The mixture is stirred for approximately 10-20 minutes at room temperature to obtain an adequate solubilization of the surfactant i.e. a homogeneous and transparent solution.

In this step, the solution of alkaline halide is, for example, sodium chloride in aqueous solution 0.1 molar, but other aqueous solutions of halides and concentrations values can be advantageously used. By way of example but not limitation, it is possible to use alkaline halides obtained by combining, in all possible ways, an alkaline cation Li, Na, K, Rb, Cs with a halide anion F, Cl, Br, I (chloride lithium, sodium chloride, potassium chloride, rubidium chloride, cesium chloride, lithium bromide, and so on), as well as their mixtures (e.g. sodium chloride and potassium bromide).

The inventors of the present invention, after long research and development, have surprisingly found that the pores diameter of the mesoporous structure (and not only that of the particle), is determined by the choice of the alkaline halide. Experimental evidence of this result is presented in the FIG. 4 and in the Example 2.

It will be apparent for those skilled in the art that in this way it has been achieved, in a new and inventive way, a method for finely tuning the size of the nanoparticles and the size of the pores in the nanoparticles mesoporous structure according to the invention. This method is advantageous, as it is well known that particles size is of paramount importance for defining the applications range especially in the biomedical field and specifically for drug delivery.

Those skilled in the art will also appreciate how the method disclosed so far represent a significant improvement of the known solutions in the technical field.

Step 2: Preparation of the Precursor Solution

The process proceeds with the preparation of a solution containing a zirconia precursor. Preferably, said precursor is zirconium iso-propoxide (in n-propanol solvent) which is mixed with ethanol in a ratio approximately equal to 1:10. However, other alkoxides precursors and/or alcoholic solvents can be advantageously used. By means of standard techniques, said mixture is stirred carefully, to ensure precursor stability, till a homogeneous solution is obtained.

Step 3: Sol-gel Reaction

The precursor solution of Step 2 is then reacted with the surfactant solution of Step 1. After the precursor solution is added dropwise to the surfactant solution, the obtained solution is thus stirred for a few hours until the sol-gel reaction is completed. Preferably said reaction is conducted at room temperature, but other temperatures can be used to accelerate the reaction kinetics as long as they are compatible with the compounds stability. After the sol-gel reaction is completed, a milky solution is obtained, which comprises a suspension of zirconia nanoparticles encapsulating the surfactant.

Step 4: Separation and Cleaning of the Nanoparticles

This step involves the separation of the zirconia nanoparticles from the milky solution obtained in the preceding step. To fully separate the nanoparticles from the solvent, well-known techniques have proved to be suitable, e.g. repeated centrifugation/washing cycles. The sediment obtained at the end of this step is then dried, preferably in air, so as to obtain a powder constituted by dried preformed nanoparticles which still encapsulate inside the surfactant.

Step 5: Solvo-thermal Treatment

The powder of dried preformed nanoparticles obtained at the end of the previous step is dispersed in a solution of ethanol and milli-Q water, preferably in a ratio of about 2:1. Said suspension is introduced into a reactor where a temperature of approximately 170° C. is maintained for about 16 hours. This treatment, called solvo-thermal, induces the extraction of the surfactant trapped in the nanoparticles, so that it is eventually obtained a solution containing the surfactant and a whitish sediment consisting of non-purified zirconia nanoparticles.

Surprisingly said nanoparticles are characterized by a spherical shape, by an amorphous structure and by pores (which fall in the mesoporous range) throughout the entire volume of the particle. In other words, the inventors have advantageously found a new and inventive method to induce the extraction of the surfactant by the zirconia nanoparticles without causing a phase transition which would lead to the formation of a non-mesoporous nanocrystalline structure having a very low specific surface area or a non-spherical shape.

The inventors have also found experimental evidence that the shape and the size of the nanoparticles as well as the shape and size of the pores can be advantageously altered or consolidated by varying the temperature and the duration of the solvo-thermal treatment.

Step 6: Separation of Nanoparticles

The process proceeds by filtering the sediment obtained previously by means, for example, of a Gooch filter or a paper filter of suitable porosity. The filtrate thus obtained is then washed with water to remove any residual salts, and finally dried in air (or also in a stove provided that the temperature is not such high to damage the structure), so as to obtain a powder consisting of nanoparticles of non-purified mesoporous zirconia nanoparticles.

Step 7: Purification of Nanoparticles

The process according to the present invention ends with the purification of the nanoparticles for removing the residual surfactant (and other solvents that may be present), so as to obtain high-purity zirconia nanoparticles characterized by a spherical shape and an amorphous totally-mesoporous structure.

Since purification techniques well-known in the state-of-the-art cannot be used (as they involve acid washing or calcination which destroy the mesoporous structure), the inventors have advantageously used a purification process based on sublimation at low temperature. Specifically, the powder previously obtained is introduces in a vacuum extraction system which is heated so as to induce sublimation of any residual surfactant and solvents.

By suitably varying the duration, temperature and pressure of the vacuum extraction system, surprisingly the sublimation-based purification process herein disclosed has proved to preserve the mesoporous structure generated in the preceding steps, and at the same time allows to produce non-cytotoxic totally-mesoporous zirconium oxide nanoparticles suitable for drug-delivery. Particularly, a temperature of about 120° C., a pressure of about $5'10^{-5}$ bar for a duration of about 12 hours allow to obtain surfactant-free medical-grade nanoparticles.

It will be apparent for those skilled in the art that the inventors have herein disclosed a new and inventive method for purifying zirconia nanoparticles that overcomes the existing limits and drawbacks of the solutions known in the art.

Through this novel variant of a sol-gel type technique, herein disclosed, it has been possible to overcome the limitations imposed by the extreme instability and reactivity of the alkoxides used as organic precursors during the synthesis of zirconia nanoparticles. It is obvious to those skilled in the art that the method may vary without departing from the basic concepts as disclosed herein. Therefore, through the implementation of the process herein disclosed has been achieved a further and important object of the present invention.

EXAMPLE Of ZIRCONIA NANOPARTICLES

By way of example, but not limitation, to follow is a disclosure of some zirconia nanoparticles obtained by means of the production method herein provided.

Example 1

Following the manufacturing method described above, the zirconia nanoparticles of FIG. 1 were prepared. The starting compounds used are the following: hexadecylamine as surfactant; sodium chloride in aqueous solution 0.1 molar as halide; zirconium isopropoxide in n-propanol as oxide precursor. All the compounds were purchased from Sigma Aldrich. Hexadecylamine and ethanol were mixed in the ratio of about 1:450. The precursor was mixed with ethanol in a ratio equal to about 1:10.

The sol-gel reaction was performed at room temperature, the reactants were stirred for about 10 hours until completion of the reaction. In the separation step, three centrifugation/washing cycles were done. The solvothermal treatment was performed at a temperature of about 170° C. for about 16 hours. The purification process by sublimation was at a temperature of about 120° C. and a pressure of about $5 \cdot 10^{-5}$ bar and lead to high-purity nanoparticles suitable for applications in the biomedical field.

With reference to the blue curve on the left side of FIG. 3 (b), such particles have a diameter of about 400 nm and pores of about 4 nm in diameter. In this sample, the measured specific surface area was 240 $m^2/g$.

Example 2

In this case, totally-mesoporous zirconia nanoparticles have been prepared starting from different halides (always in aqueous solution) than the previous example. The other process parameters were maintained essentially unchanged. Particularly, FIG. 4 presents SEM images of zirconia nanoparticles obtained, in (a) from sodium fluoride (NaF) whereas in (b) from sodium bromide (NaBr). The mean diameter of the nanoparticles is about 200 nm in the case of NaF, while about 500 nm in the case of NaBr.

The following table reports the average ionic radius of the halides and the average nanoparticles (NPs) diameters of Examples 1 and 2.

TABLE 1

| NaX- | Ionic radius (pm) | NPs. diameter (nm) |
|---|---|---|
| F | 119 | 200 |
| Cl | 167 | 400 |
| Br | 182 | 500 |

This example provides a clear demonstration that it is possible to alter the size of the particles by changing the halide during Step 1 by using the synthesis process herein disclosed, and even that there exist a correlation between the mean ionic radius of the halide anion and the mean diameters of the nanoparticles. Advantageously, by means of said correlation the halides can be selected so as to obtain particles having the desired size according to specific applications.

Example 3

In this case totally-mesoporous zirconia nanoparticles were synthesized starting first from sodium chloride (NaCl) and then from sodium iodide (NaI). The same process parameters of the Examples 1 and 2 were maintained. FIG. 3(b) shows the pore size distributions of said nanoparticles according to the BJH method, for sodium chloride (left-blue curve) and sodium iodide (right-red curve). The size of the pores are, respectively, 4 nm and 8 nm. In this case there is also an advantageous relation between the pore size and the mean ionic radius of the anion halide.

From this example it will be apparent to those skilled in the art that the manufacturing method herein disclosed, clearly allows to alter also the pores size of the particles by changing the halide during Step 1 of the synthesis process.
Description of Embodiments In the second embodiment according to the present invention, herein disclosed by way of example, but not limitation, the totally-mesoporous zirconia nanoparticles prepared through the process described above are functionalized, linked, or adsorbed with entities such as organic molecules, macromolecules, organometallic compounds or inorganic phases, so as to obtain bio-nano-systems customized according to a specific application. For example, suitable entities for NMR or optical imaging, are: magnetic iron oxides, organometallic or inorganic gadolinium compounds, organic, organometallic or inorganic coloring agents, rare earths complexes or rare earths doped oxides. Furthermore, entities such are taxol, doxorubicin or other chemotherapy drugs can be loaded in the totally-mesoporous zirconia particles so as to obtain a bio-nano system suitable for drug delivery.

Nanoparticles functionalization or loading with molecules can be accomplished by means of known techniques, which have now become standard, such as the one presented in the Example 5.

In the third embodiment of the invention according to the present invention, this also illustrated by way of example and not of limitation, the mesoporous zirconia nanoparticles are dispersed in a matrix such as a photo-curable resin, a biopolymer or other matrices whit a composition depending on the specific application. In a similar way, also bio-nano systems comprising said nanoparticles (e.g. the bio-nano systems described previously) can be dispersed in such matrices.
Industrial Applicability The novel zirconium oxide nanoparticles according to the present invention, are non-cytotoxic and are characterized by a totally-mesoporous structure. Furthermore, they can be advantageously functionalized or loaded with active molecules and entity so as to prepare a biocompatible biosystem, as well as they are easily dispersible in a medium (e.g. a biopolymer) suitable to form a biocompatible material comprising said nanoparticles and/or said nano-bio system.

These properties are highly attractive for a wide range of targeted applications in the biomedical and nanomedicine fields, where promising applications include the following:

In diagnostic or theranostic, as drug-carrier, particularly in the treatment of cancer, or contrast agent (in combination with fluorescent molecules);

In regenerative medicine and prosthetics, preparation of biocompatible scaffolds, especially in combination with bio-plotting techniques;

In dentistry, as reinforcing agent in resin-based dental fillers or in the regeneration of dental tissues;

In cosmetics, as inert filler in various cosmetic preparations, or as active filler in combination with molecules, such as UV filters or cells regeneration agents.

These applications will be more fully understood by the following Examples 4, 6, 7 and 8 which are given by way of illustration and not limitation of the present invention.

In addition, the present invention finds also application in industry, in all those applications where a high surface interaction is essential, for example in catalysis and filtration, or in sensor devices (e.g. gas sensor), just to name a few. Particularly, by exploiting the good sequestering ability of heavy metals ion, the novel zirconium oxide nanoparticles according to the present invention are useful in both groundwater treatment and process water treatment, as the following illustrative, but not limitative, Example 5, more clearly explains.

Examples of Use

Finally, form another object of the present invention the use in selected applications of the mesoporous zirconia nanoparticles according to the first embodiment of the present invention, as well as the use of the nano-bio systems and materials based on said nanoparticles according to the teachings of the second and third embodiment of the present invention.

By way of illustration, but not limitation, the following are some selected example of uses which may be implemented by those skilled in the art using well-known techniques.

Example 4

In the medical field said nanoparticles, nano-bio systems and materials can be advantageously used as diagnostic tools, contrast agents, as drug carrier or theranostic agent for the diagnosis and treatment of pathologies, particularly in the treatment of cancer.

In fact, it has been experimentally demonstrated that cells of different biological systems incorporate such totally-mesoporous zirconia nanoparticles. Specifically, the FIGS. 5(a) and (b) show confocal microscope images of a cell incorporating the nanoparticles according to the present invention: red areas show cell cytoplasm incorporating the nanoparticles labeled with Vybrants® red-fluorescent DiI lipophilic labeling solution (Life Technology, Carlsbad, Calif., USA); green areas are the cell nuclei not penetrated by the nanoparticles.

Furthermore, tests carried out according to international protocols at the Reference Center Oncology CRO of Aviano, Italy, demonstrated that the mesoporous zirconia nanoparticles are non-cytotoxic and in vivo tests on mice did not show any evident signs of toxicity. More details are available as reported by the inventors in '*Bio-compatible tailored zirconia mesoporous nanoparticles with high surface area for theranostic applications*' by Gabriele Sponchia, et al. in J. Mater. Chem. B, 2015, 3, 7300 (DOI: 10.1039/c5tb01424g).

This example provides also a demonstration that the nanoparticles according to the present invention can be easily labeled by fluorescent dye.

Example 5

The nanoparticles described in the previous examples can be used as adsorbents useful to remove from groundwater, or industrial process water, anions of heavy metals, such as Cr (VI) or other metal oxides. Due to the high specific surface area of said particles, it has been found a good adsorption in a range between about 10 mg/g to about 20 mg/g depending on the ion present in the fluid to be purified. However, the nanoparticles according to the invention are potentially able to guarantee a better adsorption capacity (higher than about 30 mg/g). In fact, the heavy metal ions sequestration capacity in particles composed of binary oxides of zirconia (e.g. $ZrO_2/TiO_2$) increases with zirconia content as Chen et al. described, for instance, in '*Facile Synthesis of Monodisperse Mesoporous Zirconium Titanium Oxide Microspheres with Varying Compositions and High Surface Areas for Heavy Metal Ion Sequestration*' (DOI: 10.1002/adfm.201102878).

Example 6

Two drugs, namely doxorubicin and irinotecan were loaded into the nanoparticles of the Example 1, following, in both cases, the following loading protocol. Firstly, a suspension of nanoparticles (about 5 mg) in an aqueous solution (about 1.5 ml) is prepared. Then a known amount of drug in a solution of known concentration (in a range between about 0.5 and about 1 mg/ml); is added to the suspension. Finally, the mixture is stirred at room temperature for 24 hours.

To verify that the drug was actually loaded into the nanoparticles, the suspension was centrifuged in order to separate the nanoparticles from the supernatant i.e. from the clear solvent phase above the nanoparticles deposit obtained after centrifugation. Analyzing the absorbance of the supernatant by means of standard techniques, the inventors estimated the amount of drug dispersed in the supernatant: the absorption signal resulted lower than that of the starting solution containing the drug, and thus the amount of drug loaded in the mesoporous nanoparticles was calculated by difference.

This control procedure has been performed at regular intervals of 6, 12, 24 and 48 hours to verify the loading time of the drug. In all cases it has been experimentally verified an excellent capacity of the totally-mesoporous zirconia nanoparticles to load doxorubicin and irinotecan with a loading capacity in a range between about 5 mg/g and about 100 mg/g.

Example 7

In the cosmetic field nanoparticles according to the present invention can be conveniently loaded with molecular or inorganic UV filters, softening agents, antioxidants and/or active ingredients for cosmetics, by means of loading protocols similar to that in the Example 6. Particularly in the treatment of bones and teeth, different loading methods can be used such the one described by Wang et al. in '*Mesoporous titanium zirconium oxide nanospheres with potential for drug delivery applications*' (DOI 10.1021/am4031104).

Furthermore, it is possible to produce multifunctional materials by dispersing, e.g. the nano-bio systems reported in Example 5, in a suitable matrix, for example biopolymers or hydrogels such as those described in '*Alginate-Based Biomaterials for Regenerative Medicine Applications*' (in Materials 2013, 6, 1285-1309; DOI:10.3390/ma6041285), or still a Room Temperature Vulcanization silicone for dental use. These multifunctional materials, in combination with bio-plotting equipment (e.g. those manufactured by EnvisionTech GmbH), are suitable for bio-printing biocompatible scaffolds for targeted applications in the field of regenerative medicine and prosthetics.

Example 8

By means of standard techniques, the nanoparticles described in Example 1, 2 and 3 can be easily dispersed in a photo-curable resin, for example in a biocompatible acrylic-based (e.g. available from 3D Systems or similar manufacturers). In this way, it is possible to produce resins loaded with biocompatible nanoparticles, useful as consumable resins for 3d-printers (or other additive manufacturing equipment) known to the state of the art for example ink-jet or material jetting equipment such as those of the series Aerosols Jet produced by Optomec Inc.

Further embodiments and advantages will be apparent to one of ordinary skill in the art in view of this specification and are all considered within the scope of the claimed invention.

In conclusion, it is apparent to those skilled in the art that the present invention fully achieved the intended aim and objects by means of the new zirconium oxide in the form of totally-mesoporous amorphous nanoparticles and the producing method thereof disclosed herein.

The invention thus conceived is susceptible of numerous modifications and variations, without departing from the basic concepts as disclosed herein. Moreover, all the details may be replaced with other technically equivalent elements. Furthermore, the order of the process steps described above is shown by way of example, but not limitation and can be changed according to convenience.

For example, in the preferred embodiment the surfactant is preferably hexadecylamine, but it can be replaced with another type of amphiphilic surfactant (ionic or nonionic); the alkaline halide is sodium chloride, but other halides can be advantageously used such as potassium (or cesium, rubidium, etc.) chloride, or sodium (or potassium, cesium, rubidium, etc.) chloride/bromide; the precursor of zirconium oxide is preferably zirconium isopropoxide but other equivalents compounds such as zirconium ethoxide or zirconium n-butoxide can be chosen; solvents (such as alcohols) and the molar concentration of the solutions containing these compounds may be modified so long as compatible with the purpose.

The above description and drawings are only illustrative of preferred embodiments which achieve the objects, features and advantages of the present invention, and it is not intended that the present invention be limited thereto. All structural, chemical, and functional equivalents to the elements of the above-described preferred embodiment that are known to those of ordinary skill in the art are expressly incorporated herein by reference and are intended to be encompassed by the present claims.

It will be appreciated that the scope of the present invention fully encompasses other embodiments which may become obvious to those skilled in the art.

Although the description and examples above contains many details, these should not be construed as limiting the scope of the invention but as merely providing illustrations of some of the presently preferred embodiments of this invention. Therefore, any modification of the present invention which comes within the spirit and scope of the following claims is considered part of the present invention.

In the appended claims, reference to an element in the singular is not intended to mean 'one and only one' unless explicitly so stated, but rather 'one or more.' Where the characteristics and techniques mentioned in any claim are followed by reference signs, those reference signs have been included for the sole purpose of increasing the intelligibility of the claims and accordingly, such reference signs do not have any limiting effect on the interpretation of each element identified by way of example, but not limitation by such reference signs.

The invention claimed is:

1. A zirconium oxide having formula $ZrO_2$ in the form of particles, wherein said particles:
   are nanoparticles or microparticles of generally spherical shape; and
   have a stable totally-mesoporous structure with a generally uniform pore distribution distributed throughout the entire volume of said particle; and
   have a specific surface area of more than about 200 $m^2/g$.

2. The zirconium oxide in the form of particles according to claim 1, wherein said particles have an average diameter ranging between about 20 nm to about 2000 nm.

3. The zirconium oxide in the form of particles according to claim 1, wherein said mesoporous structure contains pores having an average diameter ranging between about 2 nm to about 10 nm.

4. The zirconium oxide in the form of particles according to claim 1, wherein said particles are well-separated particles.

5. The zirconium oxide in the form of particles according to claim 1, wherein said particles are non-cytotoxic or substantially non-cytotoxic.

6. The zirconium oxide in the form of particles according to claim 1, wherein said particles are functionalized with or bound or adsorbed to one or more compounds selected from the group consisting of: organic molecules, macromolecules, metalorganic compounds, inorganic phases, and a combination thereof.

7. A biocompatible nano-bio system comprising:
   the zirconium oxide in the form of particles, as recited in claim 1; and
   at least one compound chemically bound or adsorbed onto one or more of said particles, said compound being selected from the group consisting of: enzymes, polypeptides, proteins, antibodies, DNA, RNA, drugs, chemotherapy drugs, chelating agents, nanoparticles, metal oxides inorganic phases, luminophore agents, fluorophore agents, photocatalyzer agents, magnetic oxides, magnetic resonance imaging agents, enhancing agents for optical imaging, and a combination thereof.

8. The biocompatible nano-bio system according to claim 7, wherein said compound is selected from the group consisting of: taxol, doxorubicin, magnetic iron oxides, inorganic or organometallic gadolinium compounds, rare earth complexes, metal oxides doped with rare earths, and a combination thereof.

9. The biocompatible nano-bio system according to claim 7, wherein said compounds are loaded in the pores of said particles.

10. A biocompatible material comprising:
    the zirconium oxide in the form of particles, as recited in claim 1; or
    a biocompatible nano-bio system comprising the zirconium oxide in the form of particles, as recited in claim 1, and at least one compound chemically bound or adsorbed onto one or more of said particles, said compound being selected from the group consisting of: enzymes, polypeptides, proteins, antibodies, DNA, RNA, drugs, chemotherapy drugs, chelating agents, nanoparticles, metal oxides inorganic phases, luminophore agents, fluorophore agents, photocatalyzer agents, magnetic oxides, magnetic resonance imaging agents, enhancing agents for optical imaging, and a combination thereof; or a combination thereof.

11. The biocompatible material according to claim 10, wherein said particles are dispersed in a matrix, said matrix being selected from the group consisting of: a resin, a photocurable resin, a polymer, a photocurable polymer, a biopolymer, an hydrogel, an oligomer, a monomer, and a combination thereof.

12. A method for producing the zirconium oxide in the form of particles as recited in claim 1, said method comprising one or more of the following steps:
    a) preparing a solution containing a surfactant, preferably hexadecylamine, and a suitable solvent, preferably ethanol, in an amount ranging between about 1:200 v/v to about 1:800 v/v;
    b) mixing the solution obtained at the end of the preceding step with an aqueous solution of an alkaline halide and stirring until a homogeneous first solution is obtained;
    c) preparing a solution containing a zirconia precursor, preferably zirconium iso-propoxide, and a suitable solvent, preferably ethanol, and stirring till a homogeneous second solution is obtained;
    d) reacting said first solution with said second solution, preferably at room temperature and for a period of time of about 10 hours, so that a third solution is obtained, said third solution containing a dispersion of zirconia particles containing said surfactant;
    e) drying, preferably air-drying, the sediment obtained after separating said zirconia particles from said third solution, so that a powder substantially composed of dried zirconia particles encapsulating said surfactant is obtained;
    f) preparing a dispersion of said dried zirconia particles in a suitable liquid, preferably ethanol and water milli-Q in a ratio of 2:1, and subject said dispersion to a thermal treatment by means of a suitable reactor so that said encapsulated surfactant is removed, and a solution containing a sediment composed of non-purified zirconia nanoparticles is obtained;
    g) filtering, washing and drying the sediment obtained at the end of the preceding step, so as to obtain a powder substantially composed of non-purified dried zirconia particles;
    h) purifying said powder by means of a purification process, so as to obtain dried purified zirconia nanoparticles characterized by a substantially spherical shape and a mesoporous amorphous structure.

13. The method according to claim 12, wherein said surfactant is selected from the group consisting of: hexadecylamine, octadecylamine, an amphiphilic ionic surfactant, an amphiphilic non-ionic surfactant, a non-ionic amine surfactant, a primary amine having an alkyl or aliphatic long chain, and a combination thereof.

14. The method according to claim 12, wherein said alkaline halide is selected from the group consisting of all possible salts resulting by a binary combinations between:
    an alkaline cation in the group consisting of Li, Na, K, Rb, Cs; and
    an halide anion in the group consisting of F, Cl, Br, I,
    or consisting of a combination of one or more of said salts, said alkaline halide being preferably sodium fluoride, sodium chloride, sodium bromide or sodium iodide, or a combination thereof.

15. The method according to claim 12, wherein in said first homogeneous solution the molar ratio between said surfactant and said alkaline halide ranges between about 0.05 to about 0.5.

16. The method according to claim 12, wherein said zirconia precursor is selected from the group consisting of: zirconium iso-propoxide, zirconium etoxide, zirconium n-butoxide, and a combination thereof.

17. The method according to claim 12, wherein the molar ratio of said second solution ranges between about 0.02 to about 0.2, preferably 0.1, with respect to the total moles of said zirconia precursor in said second homogeneous solution.

18. The method according to claim 12, wherein said thermal treatment is a solvothermal treatment taking place at a temperature between about 50° C. to about 300° C. for a period of about 1 hour to about 24 hour.

19. The method according to claim 12, wherein said purification process comprises a sublimation process, taking place under low temperature and pressure so as to extract said encapsulated surfactant, or other residual solvents, without damaging the mesoporous structure of said particles.

20. The method according to claim 19, wherein said sublimation process takes place under one or more of the following conditions:
    pressure between about $10^{-5}$ bar to about $10^{-3}$ bar;
    temperature between about 50° C. to about 150° C.;
    time period between about 240 minutes to about 600 minutes.

21. The method according to claim 12, wherein the physical properties of said particle are tunable by setting one or more of the following process parameters:
    composition of said alkaline halide;
    amount of said alkaline halide in said first solution;
    relative size of cation and anion of said alkaline halide;
    composition of said zirconium precursor;
    said physical properties being selected from the group consisting of: average diameter, shape, sphericity, pores size, pores distribution, pores shape, and a combination thereof.

22. The method according to claim 21, wherein said process parameters further include:
    amount of said zirconium precursor in said second solution;
    temperature of said solvo-thermal treatment;
    duration of said solvothermal treatment,
    and said physical properties being selected from the group consisting of: average diameter, shape, sphericity, pores size, pores distribution, pores shape, surface charge, and a combination thereof.

23. A method for drug-delivery comprising the step of using the biocompatible nano-bio system according to claim 7.

24. A method for photodynamic therapy for cancer treatment comprising the step of using the biocompatible nano-bio system according to claim 7.

25. A method for bio-imaging of biological systems, or for targeting of biological compositions comprising the step of using the biocompatible nano-bio system according to claim 7.

26. A method for regenerative medicine in combination with bio-plotting techniques or additive manufacturing advanced techniques, preferably 3d jet-printing comprising the step of using the biocompatible material according to claim 10 as a scaffold.

27. A method for using the biocompatible material according to claim 10 in dentistry or prosthesis.

* * * * *